United States Patent
Levanony et al.

(10) Patent No.: US 11,244,754 B2
(45) Date of Patent: Feb. 8, 2022

(54) ARTIFICIAL NEURAL NETWORK COMBINING SENSORY SIGNAL CLASSIFICATION AND IMAGE GENERATION

(71) Applicant: International Business Machines Corporation, Armonk, NY (US)

(72) Inventors: Dana Levanony, Tel-Aviv (IL); Tal El-Hay, Modi'in (IL); Efrat Hexter, Beit Shemesh (IL)

(73) Assignee: International Business Machines Corporation, Armonk, NY (US)

( * ) Notice: Subject to any disclaimer, the term of this patent is extended or adjusted under 35 U.S.C. 154(b) by 66 days.

(21) Appl. No.: 16/827,741

(22) Filed: Mar. 24, 2020

(65) Prior Publication Data
US 2021/0304872 A1 Sep. 30, 2021

(51) Int. Cl.
| | | |
|---|---|---|
| *G06N 3/08* | (2006.01) | |
| *G16H 30/20* | (2018.01) | |
| *G06N 3/04* | (2006.01) | |
| *G06K 9/62* | (2006.01) | |

(52) U.S. Cl.
CPC ............ *G16H 30/20* (2018.01); *G06K 9/627* (2013.01); *G06K 9/6256* (2013.01); *G06K 9/6262* (2013.01); *G06N 3/0454* (2013.01); *G06N 3/088* (2013.01); *G06K 2209/05* (2013.01)

(58) Field of Classification Search
CPC ..................................................... G16H 30/20
See application file for complete search history.

(56) References Cited

U.S. PATENT DOCUMENTS

| | | |
|---|---|---|
| 9,002,085 B1 | 4/2015 | Solanki |
| 2019/0073569 A1 | 3/2019 | Ben-Ari |
| 2021/0110254 A1* | 4/2021 | Hoang ..................... G06N 3/08 |

OTHER PUBLICATIONS

Khushboo Munir et al., "Cancer Diagnosis Using Deep Learning: A Bibliographic Review," Cancers 2019, 11, 1235.
Puspanjali Mohapatra et al., "Enhancing Histopathological Breast Cancer Image Classification using Deep Learning," International Journal of Innovative Technology and Exploring Engineering (IJITEE), vol. 8, issue 7, May 2019.
Abdullah-Al Nahid et al., "Histopathological Breast Cancer Image Classification by Deep Neural Network Techniques Guided by Local Clustering," BioMed Research International, vol. 2018.

* cited by examiner

*Primary Examiner* — Tuan H Nguyen
(74) *Attorney, Agent, or Firm* — Dvir Gassner

(57) ABSTRACT

A method which includes: Obtaining a training set which comprises: multiple data pairs each comprising: (i) a raw sensory signal acquired by a medical imaging system, and (ii) a processed image generated by the medical imaging system from the raw sensory signal; and a classification label for each of the data pairs. Based on the training set, training an artificial neural network (ANN), wherein the training comprises minimizing a global loss which is a weighted sum of: a loss between the classification labels and classification predictions by the ANN, and a similarity loss between the processed images and images generated by an intermediate layer of the ANN. The training is such that the trained ANN is configured, for a new raw sensory signal: to predict a new classification, and to generate a new image by the intermediate layer of the ANN.

20 Claims, 3 Drawing Sheets

ARTIFICIAL NEURAL NETWORK COMBINING SENSORY SIGNAL CLASSIFICATION AND IMAGE GENERATION

BACKGROUND

The invention relates to the field of artificial intelligence (AI) in medical imaging.

Traditionally, medical images are reviewed and analyzed by human experts such as radiologists, doctors, and technicians. Today, with the advent of AI technology, analysis of medical images is becoming increasingly automated, with AI algorithms being able to reliably perform tasks such as area segmentation, parameter measurement, pathology detection, and even diagnosis of various medical conditions. The use of AI in medical imagery analysis increases productivity, helps standardize processes at the medical facility, and often improves diagnosis accuracy.

Since the majority of medical images acquired today are still being manually reviewed by experts, many existing medical imaging devices, such as X-Ray machines, CT (Computerized Tomography) and MRI (Magnetic Resonance Imaging) scanners, ultrasound imagers, etc., perform image processing adjustments of the raw signals they acquire in order to make the resulting images more suited for human review. For example, many imaging devices perform automated brightness, contrast, sharpness, and/or other adjustments to the raw signal, so that the output image highlights clinically-important features—be it soft tissue, hard tissue, tumors, blood vessels, or other structures and textures. Some modern imaging devices also let their users define the medical imaging scenario or goal, and apply a different set of image processing adjustments based on the scenario of interest.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems and methods which are meant to be exemplary and illustrative, not limiting in scope.

One embodiment relates to a method comprising operating at least one hardware processor to: Obtain a training set which comprises: multiple data pairs each comprising: (i) a raw sensory signal acquired by a medical imaging system, and (ii) a processed image generated by the medical imaging system from the raw sensory signal; and a classification label for each of the data pairs. Based on the training set, train an artificial neural network (ANN), wherein the training comprises minimizing a global loss which is a weighted sum of: a loss between the classification labels and classification predictions by the ANN, and a similarity loss between the processed images and images generated by an intermediate layer of the ANN. The trained ANN is thus configured, for a new raw sensory signal: to predict a new classification, and to generate a new image by the intermediate layer of the ANN.

Another embodiment relates to a system which comprises at least one hardware processor, and a non-transitory computer-readable storage medium having program code embodied therewith, the program code executable by said at least one hardware processor to: Obtain a training set which comprises: multiple data pairs each comprising: (i) a raw sensory signal acquired by a medical imaging system, and (ii) a processed image generated by the medical imaging system from the raw sensory signal; and a classification label for each of the data pairs. Based on the training set, train an artificial neural network (ANN), wherein the training comprises minimizing a global loss which is a weighted sum of: a loss between the classification labels and classification predictions by the ANN, and a similarity loss between the processed images and images generated by an intermediate layer of the ANN. The trained ANN is thus configured, for a new raw sensory signal: to predict a new classification, and to generate a new image by the intermediate layer of the ANN.

In some embodiments, the method further comprises, or the program code is further executable by said at least one hardware processor, to: acquire the new raw sensory signal by another medical imaging system; and apply the trained ANN to the new raw sensory signals, to: predict the new classification for the new raw sensory signal, and generate the new image from the new raw sensory signal.

In some embodiments, the training set further comprises manual segmentations of distinct areas for at least some of the processed images; and the training is further to segment distinct areas in at least some of the generated new images.

In some embodiments, the distinct areas each represent at least one of: a pathology and an anatomical structure.

In some embodiments, the ANN comprises a deep neural network (DNN).

In some embodiments, the ANN comprises a generative adversarial network (GAN).

A further embodiment relates to a different system, which comprises at least one hardware processor, and a non-transitory computer-readable storage medium having program code embodied therewith, the program code executable by said at least one hardware processor to: (a) acquire a new raw sensory signal by a medical imaging system, and (b) apply an artificial neural network (ANN) to the new raw sensory signal, to: predict a new classification for the new raw sensory signal, and generate, by an intermediate layer of the ANN, a new image from the new raw sensory signal.

In some embodiment of the different system: The ANN was or is trained based on a training set which comprises: multiple data pairs each comprising: (i) a raw sensory signal acquired by another medical imaging system, and (ii) a processed image generated by the other medical imaging system from the raw sensory signal; and a classification label for each of the data pairs. The training of the ANN comprised or comprises minimizing a global loss which is a weighted sum of: a loss between the classification labels and classification predictions by the ANN, and a similarity loss between the processed images and images generated by the intermediate layer of the ANN.

In some embodiments of the different system, the training set further comprises manual segmentations of distinct areas for at least some of the processed images; and the training is further to segment distinct areas in at least some of the generated new images.

In some embodiments of the different system, the distinct areas each represent at least one of: a pathology and an anatomical structure.

In some embodiments of the different system, the ANN comprises a deep neural network (DNN).

In some embodiments of the different system, the ANN comprises a generative adversarial network (GAN).

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1:
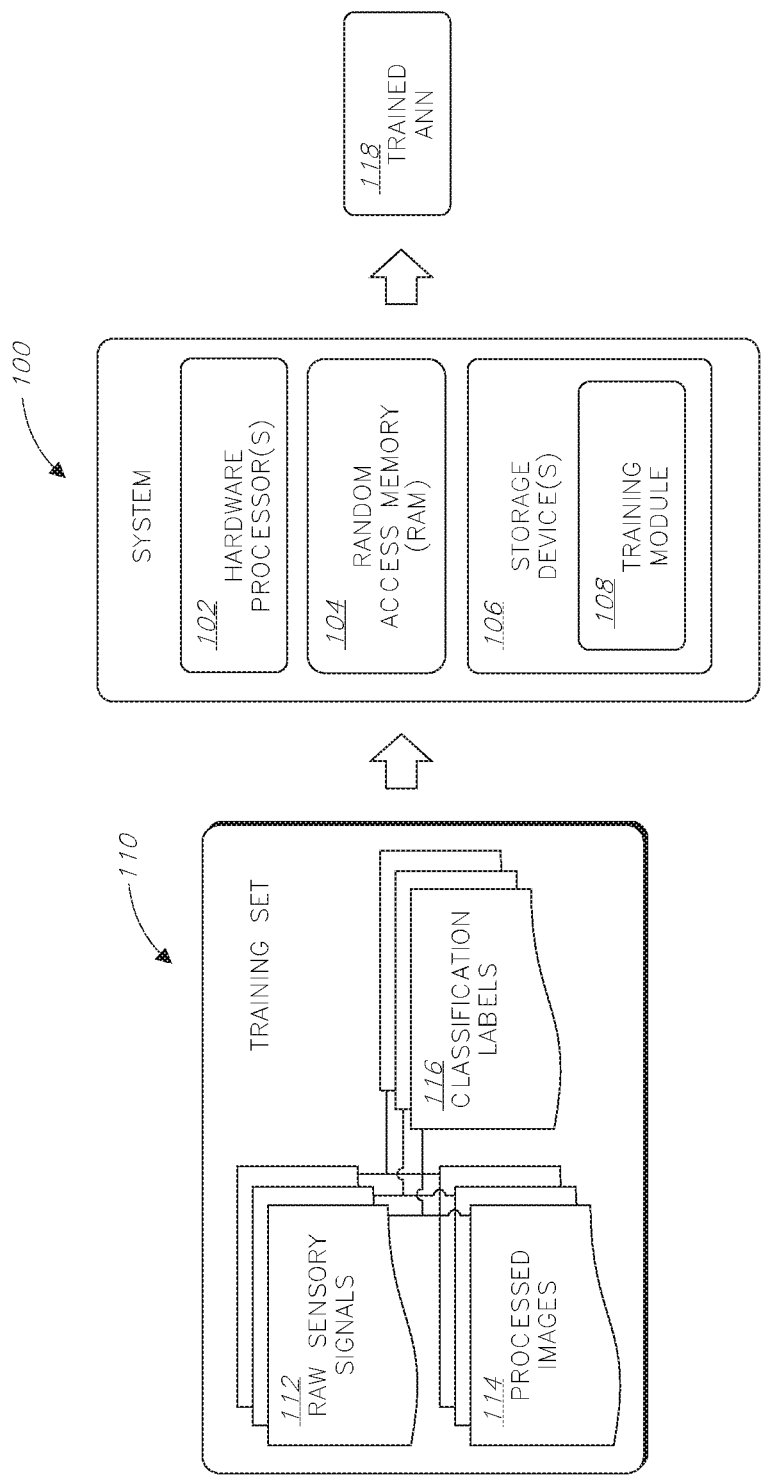
FIG. 1 is a block diagram of an exemplary system for training an artificial neural network, according to one embodiment.

Disclosed herein is an artificial neural network (ANN) that receives a raw sensory signal which was acquired by a medical imaging system, predicts a class for the signal, and generates a corresponding image which may be used for review by medical professionals as well as for archiving. Also disclosed is a method for training such ANN.

By way of example, a medical imaging system, such as an X-Ray machine, a CT scanner, an MRI scanner, a positron emission tomography (PET) scanner, a single photon emission computed tomography (SPECT) scanner, an optical coherence tomography (OCT) imager, an ultrasound imager, etc., may acquire a raw sensory signal respective of a body part of a patient. That signal, without being subject to any image processing, is provided as input to a suitably-trained ANN. The ANN processes the signal and produces the following outputs: First, a prediction of a class to which the signal (or one or more features included in it) likely belongs, such as a class denoting a certain pathology, diagnosis, anatomical parameter, clinical parameter, and/or the like. Another is a generated image, of a style similar to that commonly produced by the pertinent medical imaging system, in which the sought-after pathology and/or anatomy are depicted with sufficient clarity and enhancement. This generated image may be used in lieu of the type of image typically produced by existing medical imaging systems, which employ preset image processing steps to generate an image from the raw sensory signal.

Advantageously, these two outputs are produced by the same, single ANN, wherein the image is generated by an intermediate layer of the ANN and the class prediction by a later (such as the terminating) layer of the ANN.

To train this ANN, multiple data pairs may be used as a training set, each of these pairs including a raw sensory signal acquired by a medical imaging system, and a processed image generated by the medical imaging system from that raw sensory signal. Also included in the training set is a classification label for each of the data pairs, which was attributed to each processed image by a suitable human expert (such as a radiologist, a doctor, or a technician) who professionally reviewed that processed image; that label is used globally for each pair.

The training may include minimization of a global loss which is a sum (optionally a weighted sum) of two losses: First, a loss between the classification labels of the training set, and classification predictions made by the ANN. This ensures that the classification predictions by the ANN will be commensurate with the human expert classifications. Second, a similarity loss between the processed images and the images generated by the intermediate layer of the ANN. This ensures that the generated images depict any relevant pathology and/or anatomy with sufficient clarity and enhancement—potentially better than an image that would have been generated by the medical imaging system using standard, preset image processing steps.

A separate ANN may be trained for each imaging modality (e.g., X-Ray, CT, MRI, ultrasound, etc.), and optionally also for each medical imaging scenario (e.g., mammography, cerebral angiography, spinal imaging, etc.), to ensure that the ANN will produce reproducible results when employed with that modality and in similar medical imaging scenarios. Therefore, the training set for each ANN may be modality-specific and optionally also scenario-specific.

Reference is now made to FIG. 1, which shows a block diagram of an exemplary system 100 for training an artificial neural network, according to an embodiment. System 100 may include one or more hardware processor(s) 102, a random-access memory (RAM) 104, and one or more non-transitory computer-readable storage device(s) 106.

Storage device(s) 106 may have stored thereon program instructions and/or components configured to operate hardware processor(s) 102. The program instructions may include one or more software modules, such as a training module 108. The software components may include an operating system having various software components and/or drivers for controlling and managing general system tasks (e.g., memory management, storage device control, power management, etc.), and facilitating communication between various hardware and software components.

System 100 may operate by loading instructions of training module 108 into RAM 104 as they are being executed by processor(s) 102. The instructions of training module 108 may cause system 100 to receive a training set 110, process it, and output a trained ANN 118. Training set 110 may include: raw sensory signals 112 that were acquired by one or more medical imaging devices and did not undergo image processing; processed images 114 corresponding to the raw sensory signals 112, in a one-to-one relation; and classification labels 116 that are used globally for every pair of raw sensory signal and its processed image.

System 100 as described herein is only an exemplary embodiment of the present invention, and in practice may be implemented in hardware only, software only, or a combination of both hardware and software. System 100 may have more or fewer components and modules than shown, may combine two or more of the components, or may have a different configuration or arrangement of the components. System 100 may include any additional component enabling it to function as an operable computer system, such as a motherboard, data busses, power supply, a network interface card, a display, an input device (e.g., keyboard, pointing device, touch-sensitive display), etc. (not shown). Moreover, components of system 100 may be co-located or distributed, or the system could run as one or more cloud computing "instances," "containers," and/or "virtual machines," as known in the art.

Figure 2:
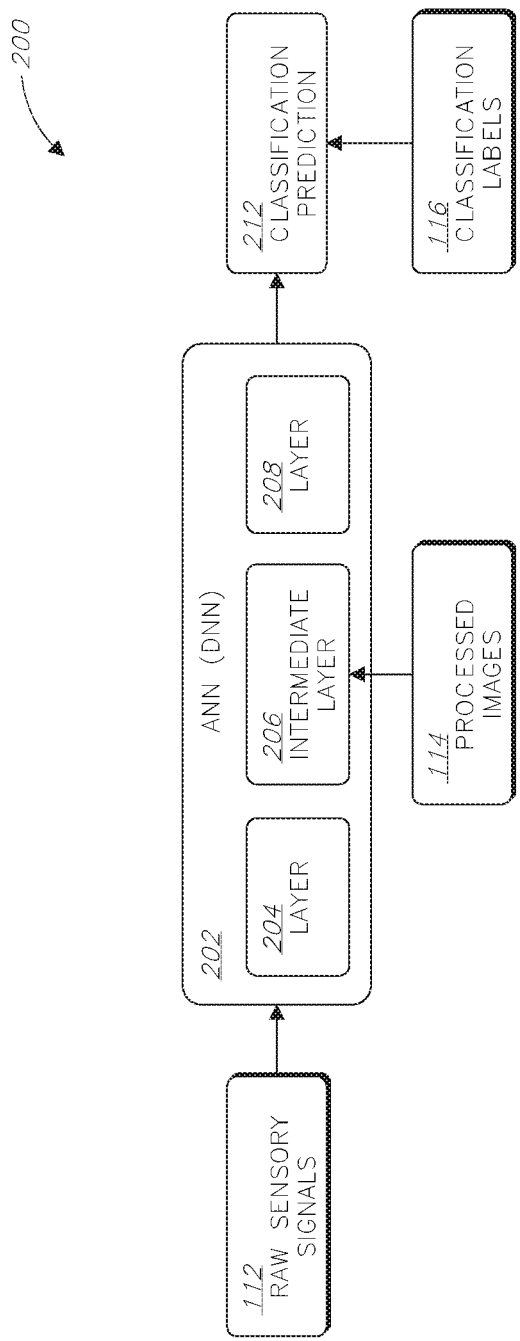
FIG. 2 is combined block diagram/flow chart illustrating a training architecture and an associated method for training the artificial neural network of FIG. 1, according to an embodiment.

The instructions of training module 108 are now discussed with reference to the combined block diagram/flow chart of FIG. 2, which illustrates a training architecture 200 and an associated method for training the ANN, in accordance with an embodiment.

First, training set 110 is obtained, which includes raw sensory signals 112, processed images 114, and classification labels 116 (all from FIG. 1). Raw sensory signals 112 may each be provided as a digital file which represents, for example, a matrix of pixels (or a grid of points in a cartesian coordinate system) and their associated sensed values. Different medical imaging system manufactures may use different formats for their raw sensory signals, and all such formats are intended herein. For medical imaging modalities that produce a series of "slices" of a three-dimensional volume (e.g., as in CT and MRI scans) or a video (e.g., as in some uses of ultrasound imaging), each "signal" of raw sensory signals 112 may in fact include a whole series of slices or a video acquired in a single imaging session of a certain patient; alternatively, such series or video may be separated into their individual slices or frames, respectively, for inclusion in training set 110.

Processed images 114, in turn, may be provided as digital image files that are the result of applying preset image processing adjustments to raw sensory signals 112 by the medical imaging system. Such adjustments may include, for example, brightness, contrast, sharpness, and/or other adjustments to raw sensory signals 112, intended by the imaging system's manufacturer to highlight clinically-important features, to de-emphasize clinically-insignificant features, and/or to otherwise make these processed images 114 more understandable to medical experts, to name a few examples.

As noted above, raw sensory signals 112 and processed images 114 are provided in the form of data pairs, each including one raw sensory signal and one processed image generated by the medical imaging system from the raw sensory signal. Classification labels 116 may be generated by one or more human experts, who review processed images 114 and decide which class each of them belongs to, such as a class denoting a certain pathology (or lack thereof), a certain diagnosis (or lack thereof), a certain quantifiable anatomical or clinical parameter (e.g., organ size/texture/location/posture of a bodily feature, behavior of a dynamic organ such as the heart or a blood vessel), and/or the like. Optionally, there is more than one classification label 116 for each of processed images 114, such as two, three, or even more labels. Examples of possible types of classification labels 116 include: "malignant" or "benign," "tumor" or "clean," "normal" or "abnormal," "stage X" or "stage Y," "herniated disc" or "bulging disc" or "normal disc," etc. Those of skill in the art will recognize many other types of classification labels that are used in the art for medical images.

Each of classification labels 116 may be used globally for one of the data pairs, because assuming it is the ground truth for one of processed images 114—it is also the ground truth for the raw sensory signal from which it was generated.

This training set 110 may then be fed to an ANN 202, such as a deep neural network (DNN) or any other suitable type of an ANN, in a training mode: Raw sensory signals 112 may be provided to a first layer 204 of ANN 202, and processed images 114 may be provided to an intermediate layer 206 of ANN 202. A terminating (last) layer 208 of ANN 202 may output classification predictions 212, which are learned to be commensurate with the provided classification labels 116. ANN 202 is shown here with three layers, but in fact may include one or more additional intermediate layers performing various required calculations.

The training of ANN 202 may be conducted as follows: a "global" loss is minimized, wherein this global loss is a sum (optionally a weighted sum) of the following: First, a loss between classification labels 116 and classification predictions 212 by the DNN. Second, a similarity loss (based on a predefined image-to-image similarity metric) between processed images 114 and images (not shown in this figure) generated by intermediate layer 206 of ANN 202.

Figure 3:
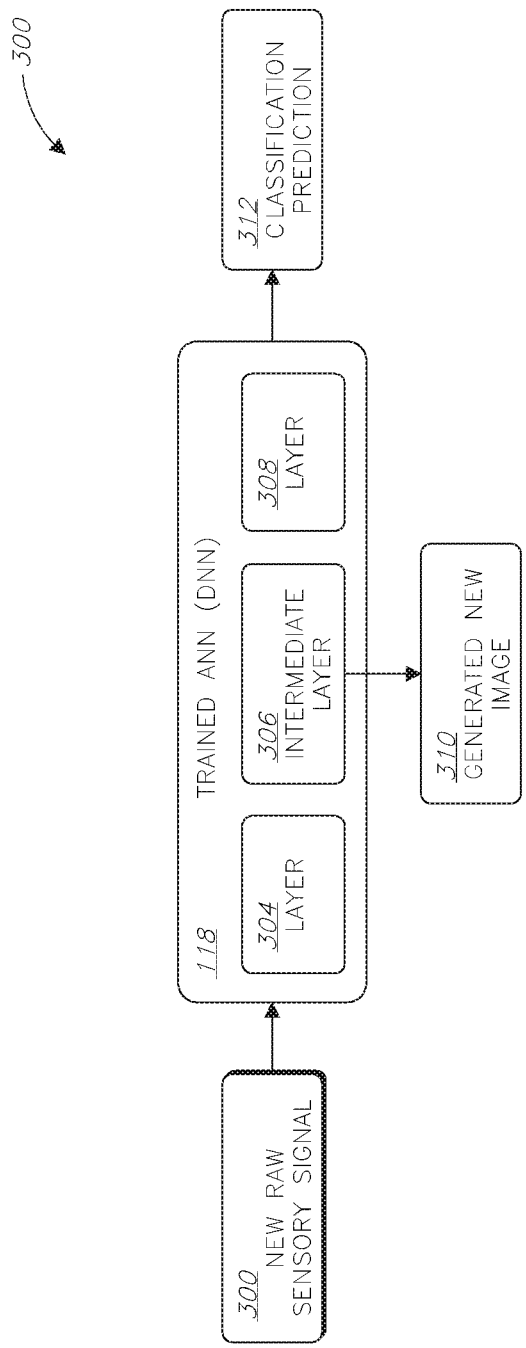
FIG. 3 is combined block diagram/flow chart illustrating an inference architecture and an associated method for classifying a new raw sensory signal and generating a new image based on that signal, according to an embodiment.

This training yields trained ANN 118 (of FIG. 1), which is now described in greater detail with reference to FIG. 3. This figure shows a combined block diagram/flow chart of an inference architecture 300 and an associated method for classifying a new raw sensory signal and generating a new image based on that signal.

A new raw sensory signal (hereinafter "new signal") 300 is acquired by another medical imaging system of the same modality, such as a system in use at a hospital, clinic, or the like. New signal 300 may then be fed to a first layer 304 of trained ANN 118, which ANN may execute on a system (not shown, for reasons of conciseness) similar to system 100 of FIG. 1, but with an inference module in lieu of training module 108.

Next, an intermediate layer 306 of trained ANN 118 generates a new image 310 that is highly likely to highlight clinically-important features, to de-emphasize clinically-insignificant features, and/or to otherwise make this new image more understandable to medical experts—potentially better than if the new raw sensory signal were to undergo preset image processing adjustments by the medical imaging system.

Lastly, a terminating (last) layer 308 of trained ANN 118 outputs a classification prediction 312 for new signal 300.

Discussed now are a number of variations of the above embodiments.

One variation is to include, in the ANN (such as in one or more layers thereof), a generative adversarial network (GAN), or a similar neural network operating according to GAN principles which are known in the art. Such GAN or similar neural network will then be responsible for generating the new images such that their statistics (i.e., transformation parameters from the new raw sensory signals to the new images) are as similar as possible to the statistics of the training set (i.e., transformation parameters from the raw sensory signals to the processed images).

Another variation is to train the ANN to also segment pathologies, anatomical structures, and/or any other distinct areas, in the images it generates. To this end, the training set may additionally include manually-annotated segmentations of the desired distinct areas appearing in the processed images; for example, segmentations of one or more pathologies (e.g., tumors, growths, foreign objects, inflammation, tissue damage, etc.), and/or anatomical structures (e.g., particular bones, spinal discs, blood vessels, organs, etc.). Then, these manual segmentations may be used as part of the ground truth of the network, and the global loss minimization may also weigh in a loss of segmentations predicted by the ANN, relative to the manually-annotated segmentations. This trained ANN will thus be able, given a new raw sensory signal, to also output (from one of its intermediate layers) a segmentation of the pertinent distinct area or an image focused on that area.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The description of a numerical range should be considered to have specifically disclosed all the possible subranges as well as individual numerical values within that range. For example, description of a range from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising operating at least one hardware processor to:
obtain a training set which comprises:
multiple data pairs each comprising: (i) a raw sensory signal acquired by a medical imaging system, and (ii) a processed image generated by the medical imaging system from the raw sensory signal, and
a classification label for each of the data pairs; and
based on the training set, train an artificial neural network (ANN), wherein the training comprises minimizing a global loss which is a weighted sum of:
a loss between the classification labels and classification predictions by the ANN, and
a similarity loss between the processed images and images generated by an intermediate layer of the ANN,
such that the trained ANN is configured, for a new raw sensory signal:
to predict a new classification, and
to generate a new image by the intermediate layer of the ANN.

2. The method of claim 1, further comprising:
acquiring the new raw sensory signal by another medical imaging system; and
applying the trained ANN to the new raw sensory signals, to:
predict the new classification for the new raw sensory signal, and
generate the new image from the new raw sensory signal.

3. The method of claim 1, wherein:
the training set further comprises manual segmentations of distinct areas for at least some of the processed images; and
the training is further to segment distinct areas in at least some of the generated new images.

4. The method of claim 3, wherein the distinct areas each represent at least one of:
a pathology and an anatomical structure.

5. The method of claim 1, wherein the ANN comprises a deep neural network (DNN).

6. The method of claim 1, wherein the ANN comprises a generative adversarial network (GAN).

7. A system comprising:
at least one hardware processor; and
a non-transitory computer-readable storage medium having program code embodied therewith, the program code executable by said at least one hardware processor to:
(a) obtain a training set which comprises:
multiple data pairs each comprising: (i) a raw sensory signal acquired by a medical imaging system, and (ii) a processed image generated by the medical imaging system from the raw sensory signal, and
a classification label for each of the data pairs, and
(b) based on the training set, train an artificial neural network (ANN), wherein the training comprises minimizing a global loss which is a weighted sum of:
a loss between the classification labels and classification predictions by the ANN, and
a similarity loss between the processed images and images generated by an intermediate layer of the ANN,
such that the trained ANN is configured, for a new raw sensory signal:
to predict a new classification, and
to generate a new image by the intermediate layer of the ANN.

8. The system of claim 7, wherein the program code executable by said at least one hardware processor to:
acquire the new raw sensory signal by another medical imaging system; and
apply the trained ANN to the new raw sensory signals, to:
predict the new classification for the new raw sensory signal, and
generate the new image from the new raw sensory signal.

9. The system of claim 7, wherein:
the training set further comprises manual segmentations of distinct areas for at least some of the processed images; and
the training is further to segment distinct areas in at least some of the generated new images.

10. The system of claim 9, wherein the distinct areas each represent at least one of:
a pathology and an anatomical structure.

11. The system of claim 7, wherein the ANN comprises a deep neural network (DNN).

12. The system of claim 7, wherein the ANN comprises a generative adversarial network (GAN).

13. A system comprising:
at least one hardware processor; and
a non-transitory computer-readable storage medium having program code embodied therewith, the program code executable by said at least one hardware processor to:
(a) acquire a new raw sensory signal by a medical imaging system, and
(b) apply an artificial neural network (ANN) to the new raw sensory signal, to:
predict a new classification for the new raw sensory signal, and
generate, by an intermediate layer of the ANN, a new image from the new raw sensory signal.

14. The system of claim 13, wherein:
the ANN was trained based on a training set which comprises:
multiple data pairs each comprising: (i) a raw sensory signal acquired by another medical imaging system, and (ii) a processed image generated by the other medical imaging system from the raw sensory signal, and
a classification label for each of the data pairs,
the training of the ANN comprised minimizing a global loss which is a weighted sum of:
a loss between the classification labels and classification predictions by the ANN, and
a similarity loss between the processed images and images generated by the intermediate layer of the ANN.

15. The system of claim 14, wherein:
the training set further comprises manual segmentations of distinct areas for at least some of the processed images; and
the training is further to segment distinct areas in at least some of the generated new images.

16. The system of claim 15, wherein the distinct areas each represent at least one of: a pathology and an anatomical structure.

17. The system of claim 14, wherein the ANN comprises a deep neural network (DNN).

18. The system of claim 14, wherein the ANN comprises a generative adversarial network (GAN).

19. The system of claim 13, wherein the ANN comprises a deep neural network (DNN).

20. The system of claim 13, wherein the ANN comprises a generative adversarial network (GAN).

* * * * *